United States Patent
Zhang et al.

(10) Patent No.: US 10,336,606 B2
(45) Date of Patent: Jul. 2, 2019

(54) INTEGRATED CAPACITIVE HUMIDITY SENSOR

(71) Applicant: Freescale Semiconductor, Inc., Austin, TX (US)

(72) Inventors: Qing Zhang, Montreal (CA); Mohommad Choudhuri, Brossard (CA); Gul Zeb, Montreal (CA)

(73) Assignee: NXP USA, Inc., Austin, TX (US)

( * ) Notice: Subject to any disclaimer, the term of this patent is extended or adjusted under 35 U.S.C. 154(b) by 127 days.

(21) Appl. No.: 15/053,456

(22) Filed: Feb. 25, 2016

(65) Prior Publication Data
US 2017/0247247 A1    Aug. 31, 2017

(51) Int. Cl.
| | | |
|---|---|---|
| *H01L 27/14* | (2006.01) | |
| *H01L 27/085* | (2006.01) | |
| *B81B 7/00* | (2006.01) | |
| *B81C 1/00* | (2006.01) | |
| *G01N 27/22* | (2006.01) | |

(52) U.S. Cl.
CPC .......... *B81B 7/008* (2013.01); *B81C 1/00246* (2013.01); *G01N 27/223* (2013.01); *B81B 2201/0214* (2013.01); *B81B 2207/015* (2013.01); *B81B 2207/07* (2013.01); *B81C 2201/016* (2013.01); *B81C 2201/019* (2013.01); *B81C 2201/0159* (2013.01)

(58) Field of Classification Search
CPC .............. G01N 27/226; G01N 27/227; G01N 27/4141; G01N 27/4148; B81B 7/008; B81B 2207/015; B81B 2207/07; B81B 2201/0214; B81C 1/00246

USPC ......................................................... 438/49
See application file for complete search history.

(56) References Cited

U.S. PATENT DOCUMENTS

| | | | |
|---|---|---|---|
| 8,852,983 B1 | 10/2014 | Fedder et al. | |
| 2004/0008471 A1* | 1/2004 | Davis | G01D 5/24 361/306.3 |
| 2005/0097941 A1* | 5/2005 | Sandvik | G01N 27/4141 73/31.06 |
| 2005/0188764 A1* | 9/2005 | Itakura | G01N 27/223 73/335.04 |
| 2006/0001116 A1* | 1/2006 | Auburger | B81B 7/0067 257/433 |
| 2006/0037404 A1* | 2/2006 | Watanabe | G01N 27/223 73/714 |
| 2006/0103018 A1* | 5/2006 | Bureau | C25D 9/02 257/734 |
| 2006/0238290 A1* | 10/2006 | Arisaka | G01N 27/225 338/35 |

(Continued)

OTHER PUBLICATIONS

Electrografting: a powerful method for surface modification, Chemical Society Reviews 40(7):3995-4048 Jul. 2011.*

(Continued)

*Primary Examiner* — Sheikh Maruf

(57) ABSTRACT

A semiconductor device composed of a capacitive humidity sensor comprised of a moisture-sensitive polymer layer electrografted to an electrically conductive metal layer situated on an CMOS substrate or a combined MEMS and CMOS substrate, and exposed within an opening through a passivation layer, packages composed of the encapsulated device, and methods of forming the capacitive humidity sensor within the semiconductor device, are provided.

12 Claims, 13 Drawing Sheets

(56) References Cited

U.S. PATENT DOCUMENTS

| | | | | |
|---|---|---|---|---|
| 2009/0141767 A1* | 6/2009 | Cummins | ............ | G01N 27/223 374/142 |
| 2009/0273009 A1* | 11/2009 | Cummins | ............ | G01N 27/223 257/252 |
| 2010/0327429 A1* | 12/2010 | Ou | ............ | H01L 21/568 257/698 |
| 2011/0088456 A1* | 4/2011 | Ren | ............ | G01N 33/005 73/31.06 |
| 2011/0303953 A1* | 12/2011 | Kamata | ............ | H01L 27/12 257/253 |
| 2012/0000285 A1* | 1/2012 | Waga | ............ | G01N 27/225 73/335.04 |
| 2012/0211845 A1* | 8/2012 | Daamen | ............ | B81C 1/00246 257/414 |
| 2013/0207673 A1* | 8/2013 | Tondokoro | ............ | G01N 27/223 324/664 |
| 2013/0327649 A1* | 12/2013 | Polesel Maris | ............ | G01N 29/022 205/91 |
| 2013/0328142 A1* | 12/2013 | Nackaerts | ............ | H01L 29/84 257/415 |
| 2014/0070337 A1* | 3/2014 | Besling | ............ | H01L 21/77 257/415 |
| 2014/0077314 A1* | 3/2014 | Humbert | ............ | G01N 27/227 257/414 |
| 2014/0077824 A1* | 3/2014 | Niimi | ............ | G01N 27/121 324/664 |
| 2014/0196522 A1* | 7/2014 | Borini | ............ | G01N 7/00 73/29.03 |
| 2014/0197500 A1 | 7/2014 | Guillemet et al. | | |
| 2014/0295605 A1 | 10/2014 | Fedder et al. | | |
| 2015/0047430 A1* | 2/2015 | Benzel | ............ | G01N 27/225 73/335.04 |
| 2015/0122050 A1* | 5/2015 | Kono | ............ | G01F 1/692 73/861.08 |
| 2015/0180452 A1 | 6/2015 | Sundareswaran et al. | | |
| 2016/0023888 A1* | 1/2016 | Quevy | ............ | H05K 999/99 257/414 |
| 2016/0202201 A1* | 7/2016 | Cobianu | ............ | G01N 27/223 73/335.04 |
| 2016/0236932 A1* | 8/2016 | Chau | ............ | B81C 1/00246 |
| 2016/0266061 A1* | 9/2016 | Yu | ............ | G01L 19/0092 |
| 2017/0167875 A1* | 6/2017 | Bhandari | ............ | G01C 19/5776 |

OTHER PUBLICATIONS

S. Pang et al., Journal of Atmospheric and Oceanic Technology, vol. 13, 1110-1115, Oct. 1996.

H. Farahani et al., Sensors 2014, 14, 7881-7939.

Matsuguchi et al., J. Electrochem. Soc., vol. 141, No. 3, Mar. 1994, pp. 614-618.

Matsuguchi et al., J. Electrochem. Soc., vol. 138, No. 6, Jun. 1991, pp. 1862-1865.

Quinton et al., Surface & Coatings Technology 206 (2012), 2302-2307.

Belanger et al., Chem. Soc. Rev., 2011, 40, 3995-4048.

Charlot, Aurelia et al; "Combination of Electrografting and Layer-by-Layer Deposition: An Efficient Way to Tailor Polymer Coatings of (semi)-Conductors"; Chemical Communications Chemcom., No. 44; p. 4656-4658.

Cornila, C. et al; "Capacitive Sensors in CMOS Technology with Polymer Coating"; Sensors and Actuators B: Chemical: International Journal Devoted to Research and Development of Physical and Chemical Transducers, vol. 25, No. 1-3; Elsevier BV, NL: pp. 357-361 (Apr. 1, 1995).

* cited by examiner

INTEGRATED CAPACITIVE HUMIDITY SENSOR

FIELD OF THE DISCLOSURE

The present disclosure relates generally to structures for chemical sensing and, more particularly, to a capacitive humidity sensor integrated, for example, into a complementary metal oxide semiconductor (CMOS) substrate or like structure.

BACKGROUND OF THE DISCLOSURE

In many automated industrial processes and climate control systems, it is often necessary to sense and control the ambient humidity level. Capacitive relative humidity sensors are widely used in various areas of applications such as instrumentation, automated systems and climatology, to monitor and detect humidity levels.

Humidity sensors utilize changes in the physical and electrical properties of a sensitive material (e.g., dielectric polymer) when exposed to atmospheric humidity conditions of a surrounding area. In principle, with a capacitive type organic polymer film humidity sensor, the absorbed water vapor occupies free spaces between polymer molecules, and the dielectric permittivity of the polymer is linearly changed proportionally to the amount of absorbed water. Capacitive type humidity sensors thus provide a measure of the humidity based on the amount of absorption or desorption of water molecules and the resultant variation of the dielectric constant of the sensing material, and thus changes in its capacitance. Thus, humidity changes are directly detected by measuring the changes of the capacitance of the sensing material.

In general, the typical configuration of a capacitance sensor is either a sandwich structure with two electrode surfaces on each side, or an interdigitated structure with comb electros and the sensing material (e.g., dielectric polymer) deposited inbetween.

Various attempts have been made to integrate humidity and other chemical capacitance sensors into CMOS structures. For example, capacitive humidity sensors have been fabricated by forming a bottom electrode, depositing a chemical-sensitive polymer layer (e.g., polyimide), and then patterning a set of top electrodes (e.g., conductors). However, this structure is difficult to integrate with testing electronics. In addition, placing the sensitive material layer between two metal layers requires significant processing beyond conventional CMOS.

Another attempt involved coating interdigitated metal electrodes with a chemical-sensitive polymer. While this approach eliminated the necessity of having metal above and below the sensitive layer, a large, parallel capacitance was created through the substrate under the electrodes.

Another technique to produce an integrated chemical capacitance sensor into a CMOS structure involved selectively etching the dielectric of the CMOS to expose a core metal layer (electrically connected in series between two other metal adhesion layers). The exposed core metal layer is then etched to form a cavity between the two metal adhesion layers. The cavity is then filled with an environmental-sensitive dielectric material that is capable of selectively absorbing the chemical to be sensed. For humidity applications, polymers such as polyimide, polymethylmethacrylate (PMMA), poly(ethylene terephthalate) (PET), polysulfone (PSF), cellulose acetate butyrate (CAB) and polyethynyl fluorenol (PEFI), are used. The metal adhesion layers then act as the top and bottom electrodes of the environmental-sensitive capacitor. However, this method requires the modification of the CMOS process flow to accommodate the incorporation of humidity sensor.

BRIEF DESCRIPTION OF THE DRAWINGS

Example embodiments of the present invention are illustrated by way of example and are not limited by the accompanying figures, in which like references indicate similar elements. Elements in the figures are illustrated for simplicity and clarity and have not necessarily been drawn to scale.

DETAILED DESCRIPTION

Example embodiments of the disclosure generally include semiconductor devices, packaged devices, and methods for forming the devices and packages. The illustrated example embodiments correspond to the formation of semiconductor devices in the form of a CMOS device which is structured with a capacitive humidity sensor on an integrated circuit (IC) substrate (e.g., a CMOS substrate) according to various example embodiments of the disclosure. In example embodiments, the capacitive humidity sensor is formed by electrografting a moisture-sensitive polymer to a metal substrate layer.

The present disclosure provides an improved method for integrating a capacitance-based humidity sensor into a CMOS structure using a post-CMOS approach. In addition, with the direct connection of MEM substrates to CMOS substrates through wafer bonding, example embodiments of the disclosure can be used to integrate humidity sensors onto such MEMS-CMOS substrates to achieve microsystems that have enhanced functionalities. Thus, in example embodiments, the disclosed process flows can integrate the fabrication of a humidity sensor on MEMS and CMOS substrates.

Figure 1:
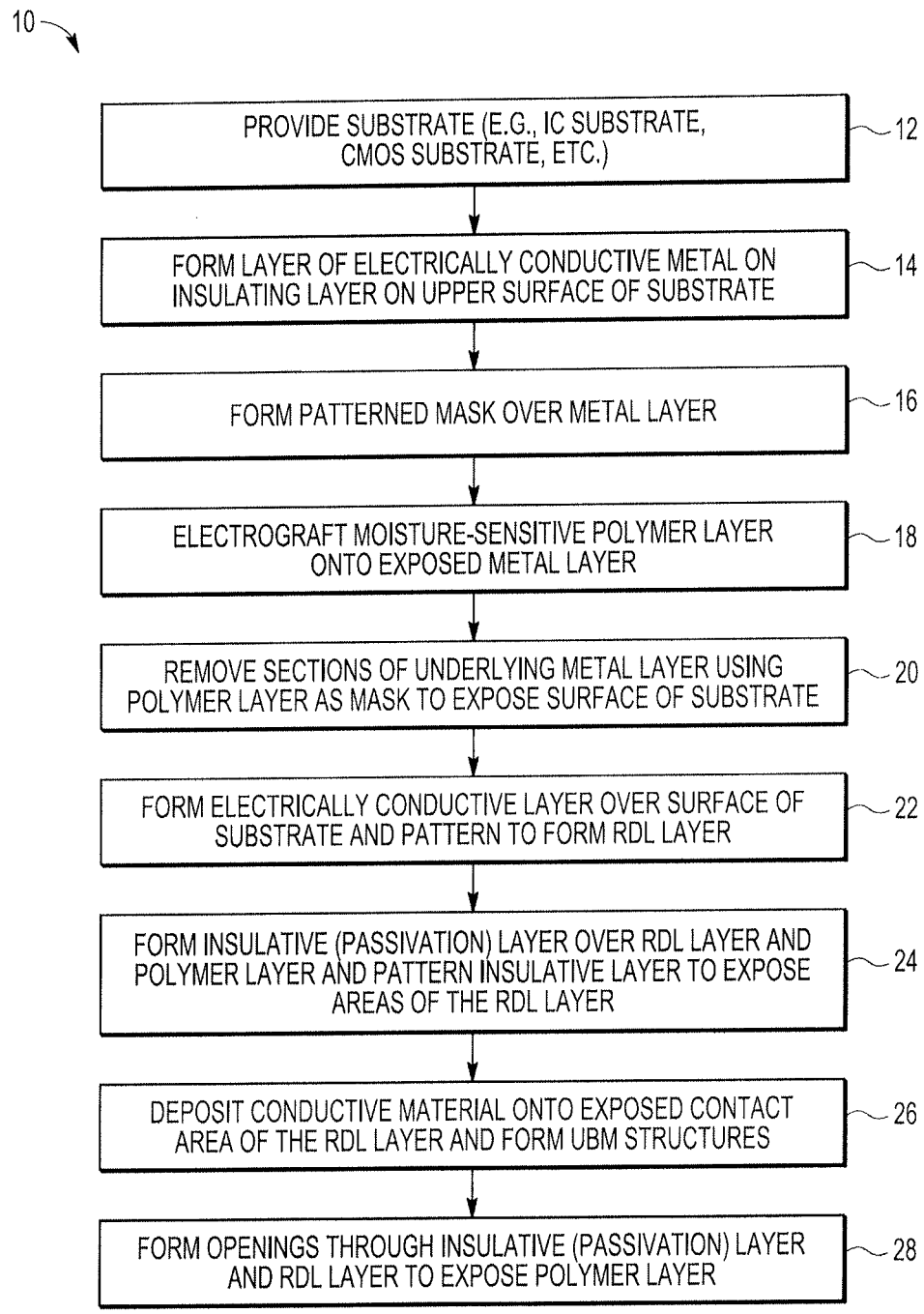
FIG. 1 is flow diagram illustrating a fabrication sequence to construct a capacitive humidity sensor according to an example embodiment of the invention, given by way of example.
Figure 2:
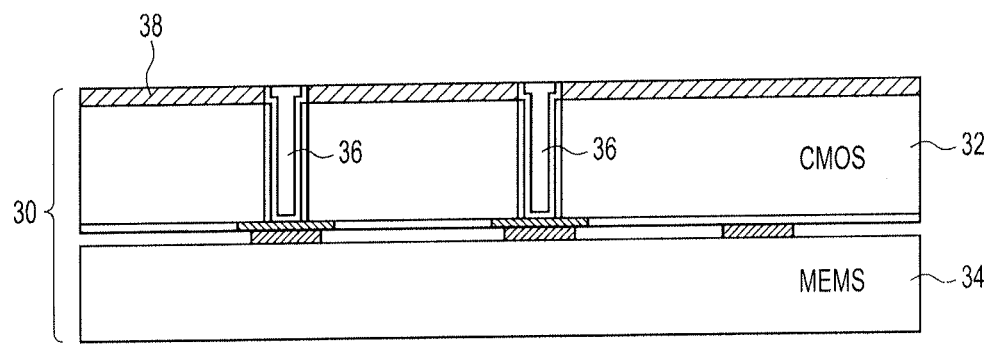
FIG. 2 is a cross-sectional, elevational view of an exemplary substrate for use in the procedure illustrated in FIG. 1.

FIG. 1 is a flowchart showing an example embodiment of a procedure 10 for fabricating a capacitive humidity sensor on an integrated circuit (IC) substrate according to example embodiments of the present disclosure. In example embodiments, the procedure is a low-temperature process conducted at a maximum temperature of 300° C. FIGS. 2 to 11 illustrate views of a semiconductor device at various stages of manufacture according to the process flow shown in FIG. 1.

The fabrication procedure 10 commences at block 12 where a substrate 30 (FIG. 2) is provided. As illustrated, in example embodiments, the substrate 30 can be the form of a complementary metal oxide semiconductor (CMOS) substrate 32 bonded to a microelectromechanical systems (MEMS) substrate 34. In another example embodiment, the MEMS substrate 34 is absent. As shown, the CMOS substrate 32 is structured with an insulating layer 38 (e.g., silicon oxide, SiO) on an upper surface. In example embodiments, the CMOS substrate 32 can include a plurality of conductive through-silicon vias (TSVs) 36 that extend therethrough. The conductive TSVs can be formed, for example, from copper, using known methods. Electrical contacts can then be made to the CMOS substrate through these TSVs.

Figure 3:
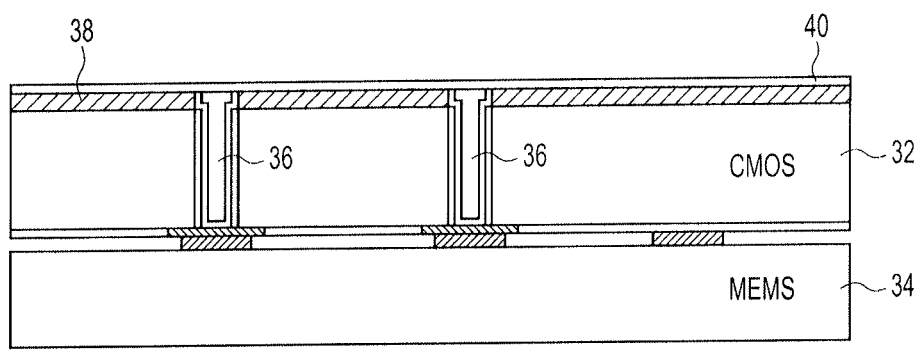
FIG. 3 is a cross-sectional, elevational view of the substrate of FIG. 2, at a subsequent process step according to the operational sequence of FIG. 1, showing the deposition of an electrically conductive metal layer on the substrate.

Next, at block 14 (FIG. 1), a conductive metal layer 40 is formed on the insulating layer 38 on the upper surface of the CMOS substrate 32, as illustrated in FIG. 3. The metal layer 40 is electrically connected to one or more TSVs. In example embodiments, the conductive metal layer 40 is an inert metal being chemically inert or unreactive to the reagents used in the composition (e.g., solvents, acidic component, etc.) in the electrografting process. In example embodiments, the metal layer 40 functions as the bottom electrode of the capacitive humidity sensor.

In various example embodiments, the conductive metal layer can be formed from titanium (Ti), platinum (Pt), gold (Au), or another electrically conductive material to which an organic material layer (e.g., polymer layer) can be attached through an electrografting procedure as further described herein. In various example embodiments, the conductive metal layer 40 is compatible with an aqueous acidic composition applied in the electrografting process to attach the organic polymer layer thereto. The conductive metal layer 40 can be formed by any appropriate processing technique (e.g., physical vapor deposition (PVD) or sputtering, etc.). In example embodiments, the maximum temperature at which block 14 (FIG. 1) is performed is 200° C.

The operational sequence of the process of FIG. 1 progresses to block 16 where a patterned mask 42 (FIG. 4) such as a photoresist or other type of patternable material that can be selectively removed, is formed over the conductive metal layer 40. The mask 42 includes openings exposing the areas 44 of the metal layer on which an organic layer (e.g., polymer layer) is to be electrografted, and one or more electrical contact areas 46 at an edge 46 of the substrate 32. The maximum temperature at which block 16 (FIG. 1) should be performed is 120° C.

Figure 5:
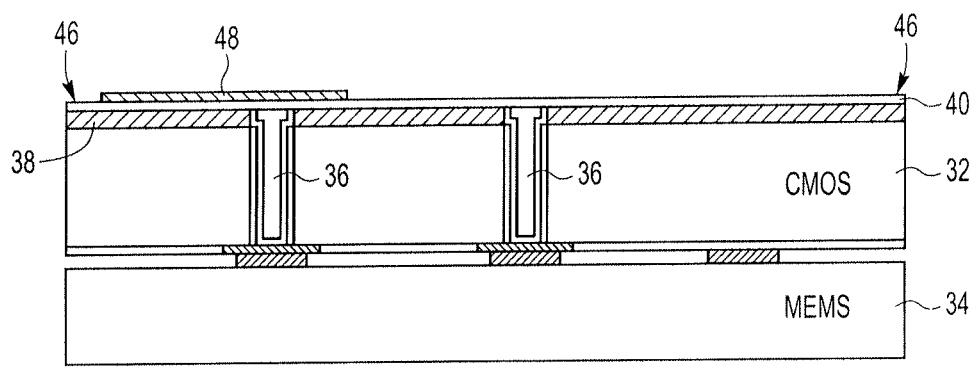
FIG. 5 is a cross-sectional, elevational view of the substrate of FIG. 4, at a subsequent process step according to the operational sequence of FIG. 1, showing the formation of an organic (polymer) layer on the electrically conductive metal layer by an electrografting process.

Next, at block 18 (FIG. 1), an organic layer 48 is formed on the unmasked, exposed area 44 of the electrically conductive metal layer 40 by an electrografting process, as depicted in FIG. 5. In the illustrated example embodiment, the organic layer 48 is a moisture sensitive, dielectric polymer layer. Electrografting generally refers to an electrochemically initiated chemical grafting process whereby an organic layer (e.g., polymer layer) is attached to a solid conducting substrate such as a metal layer.

Examples of suitable polymers as the polymer layer 48 in a capacitive humidity sensor according to the disclosure, which have a sensitivity to water vapor (humidity), include polyvinyl esters such as polyvinyl methacrylate (PVM), polyvinyl benzoate (PVG), polyvinyl crotonate (PVCr), polyvinyl cinnamate (PVCi), and polymethyl methacrylate (PMMA), among others. In an example embodiment, the polyvinyl ester polymer is polyvinyl benzoate, polyvinyl cinnamate and polyvinyl methacrylates. In example embodiments, the polymer (e.g., polyvinyl ester) can incorporate functional groups such as carboxyl (—COOH), hydroxyl (—OH) or amino (—NH$_2$) groups, among others. Such substituents and/or functional groups provide cross-linking of polymer chains via dehydration, esterification, peptidation or other reaction involving the functional groups.

Figure 6:
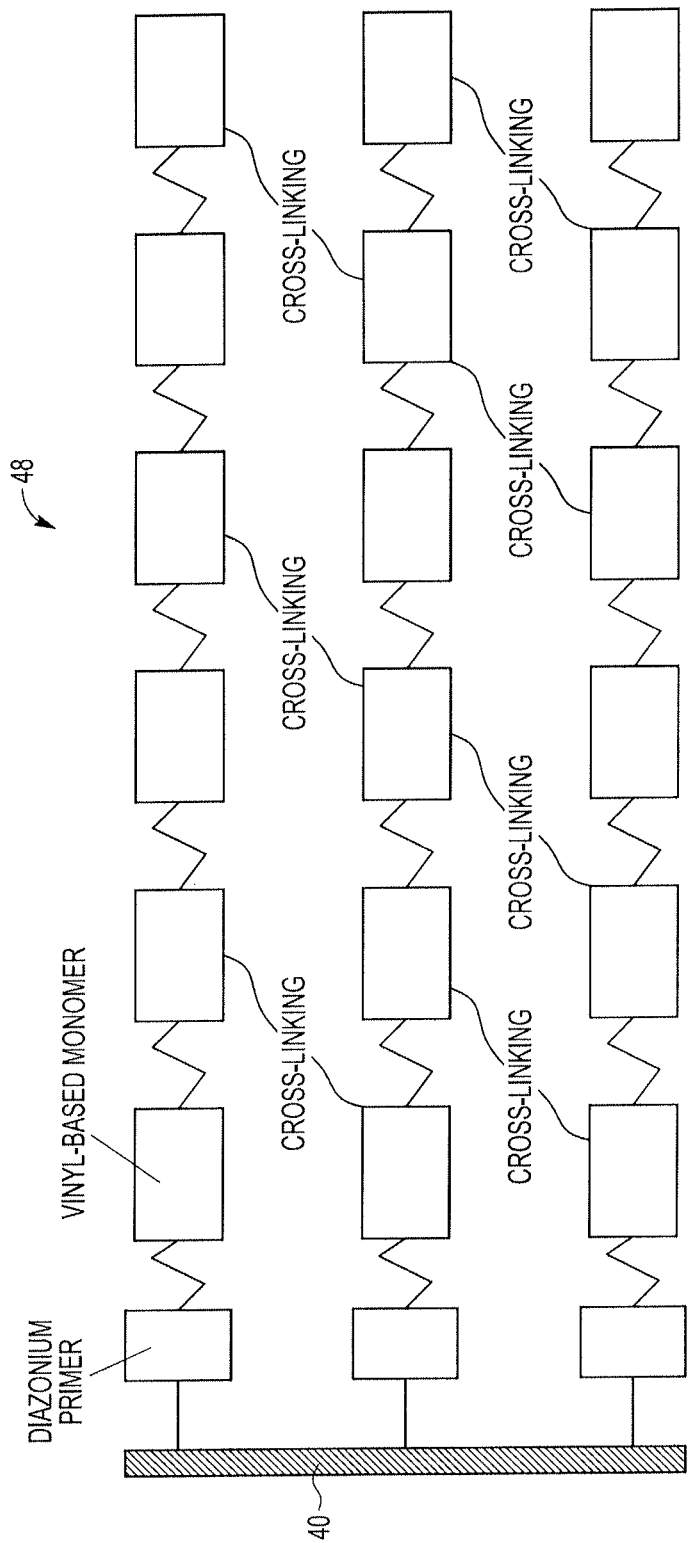
FIG. 6 is diagrammatic representation of an example embodiment of the configuration of an electrografted polymer attached to the electrically conductive metal layer.

In an example embodiment, in a first step in the electrografting process, a primer layer is chemically bonded to the exposed surface of the metal layer 40 to functionalize the metal layer with reactive groups. The primer layer then initiates the polymerization of monomers (e.g., vinyl monomers) through the formation of initial primer-monomer bonds that will then anchor a network of polymer chains onto the surface of the metal layer 40, as illustrated in FIG. 6.

In various example embodiments, the electrografting process comprises electroreduction of an aryldiazonium salt or a vinyl compound in an aqueous acidic solution or in an organic solvent in the presence or absence of a cross-linking agent. For example, with a polyvinyl ester such as polyvinylbenzoate, polyvinyl cinnamate, and polyvinyl chrotonate, among others, which have carboxyl (—COOH), hydroxyl (—OH) and/or amino (—NH$_2$) functional groups on adjacent polymer chains, internal cross-linking can occur during a post-electrografting anneal without the use of an added cross-linking agent. In other example embodiments, a cross-linking agent (e.g. divinyl benzene, ethylene glycol, etc.) can be added to the composition to introduce desired cross-linking, for example, of polymethyl methacrylate-type polymers.

In various example embodiments, the organic solvent can be, for example, acetonitrile, dimethylformamide (DMF), propylene carbonates, dichloromethane, or other suitable organic solvents that fulfill both solubility and specific solvent potential window criteria for use in electrochemical processes including electrografting of aryldiazonium salts and vinyl compounds, among others.

Examples of aryldiazonium salts include benzenediazonium, 4-carboxybenzenediazonium, 4-nitrobenzenediazonium, 4-acetamidobenzenediazonium, 4-bromobenzenediazonium, napthalenediazonium, and nitronapthalenediazonium, among others.

In general, all vinyl compounds mentioned herein can be used for general electrografting purposes. For application in humidity sensors, suitable vinyl compounds include, for example, vinyl methacrylates (e.g. vinyl hydroxymethylmethacrylate, vinyl carboxymethylmethaerylate, vinyl aminomethylmethacrylate, etc.), vinyl benzoates (e.g. vinyl hydroxybenzoate, vinyl carboxybenzoate, vinyl aminobenzoate, etc.), vinyl cinnamates (e.g. vinyl hydroxycinnamate, vinyl carboxycinnamate, vinyl aminocinnamate, etc.), vinyl chrotonate, (meth)acrylates (e.g., butyl methacrylate, hydroxymethyl methacrylate, etc.), and ethyl acrylates (e.g., 2 chloropropionate ethyl acetate, etc.).

In example embodiments, the electrografting composition includes an inorganic acid such as hydrochloric acid (HCl), sulfuric acid (H$_2$SO$_4$), and phosphoric acid (H$_3$PO$_4$), among others. In example embodiments, the amount of acid included in the solution is sufficient to provide an acidic condition for stability of diazonium salts in an aqueous solution. In example embodiments, the amount of acid in the solution is sufficient to provide a pH in the range of 1 to 2.

In various example embodiments, the electrografting composition is an aqueous solution comprising water, a vinyl monomer, an aryldiazonium cation, an inorganic acid (e.g., HCl or H$_2$SO$_4$). In an example embodiment, the electrografting composition is an aqueous solution comprising water, 0.3 to 0.7 M vinyl monomer, 0.01 to 0.02 M aryldiazonium cation, and 0.01 to 0.1 M inorganic acid (e.g., HCl or H$_2$SO$_4$).

Figure 4:
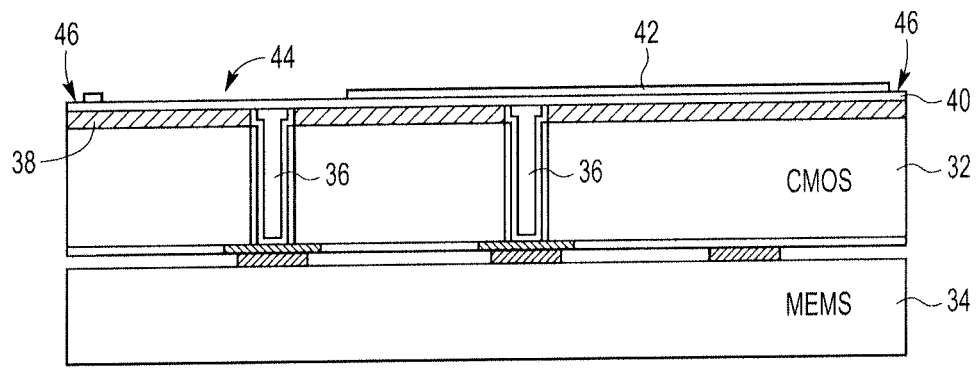
FIG. 4 is a cross-sectional, elevational view of the substrate of FIG. 3, at a subsequent process step according to the operational sequence of FIG. 1, showing the formation of a photomask onto the electrically conductive metal layer.

Electrografting process will be performed on the exposed area 44 of the metal layer 40 on the assembly shown in the FIGS. 4 and 5. An electrochemical cell for carrying out this electrografting process will be composed of (i) a working electrode, which in the illustrated example embodiment, is the metal layer 40 (including the whole assembly as shown in the FIG. 5), (ii) a counter electrode of inert platinum (Pt) or suitable platinized metal (an external system to complete the electric circuit for electrografting; not a component of the assembly shown in FIG. 5), (iii) the electrografting solution applied between the working and the counter electrode, and (iv) an external power supply providing desired electrical potentials to the metal layer 40 (working electrode) through contact points 46 and to the external counter electrode (Pt or platinized metal).

In an example embodiment, the electrografting solution/composition can be prepared by mixing individual components (e.g., vinyl monomer, aryldiazonium cation and acidic components) in a dedicated mixing system (e.g., mixing chamber, beaker, etc.). The electrografting composition can then be applied between the working and counter electrodes by using appropriate transfer system (e.g., beaker, other transfer vessel or apparatus).

In example embodiments, the electrografting process can be conducted by applying a desired potential (using an external power supply) for a specific period of time across the working and counter electrodes through the electrografting composition or solution (e.g., containing vinyl monomer, aryldiazonium cation and acidic components), whereby electroreduction of the diazonium cation (ArN$_2^+$) from the solution forms aryl radicals.

Aryl radicals formed by the electroreduction of the diazonium salt from the solution, chemically bond on one side to the surface of the metal layer 40 to form a primer layer (e.g., monolayer) of the aryl radicals, as illustrated in FIG. 6. On the other side, the aryl radicals initiate the polymerization of the vinyl compound which initially attach to the primer layer of aryl radicals. The polymerization reaction is continued to form the polymer layer 48. In example embodiments, the electrografting reaction leads to a layer of the polyvinyl ester polymer on top of a primer layer bonded to the surface of the metal layer 40. In example embodiments, the polymer layer can be rinsed to remove unattached polymer. The thickness of the polymer layer 48 can vary depending, for example, on the nature of the polymer, duration of the electrografting process, and on the specific use or purpose of the final device. In example embodiments, the polymer layer 48 ranges in thickness from 100 to 300 nm.

The electrolysis can be performed by applying an electrical potential of −1V/SCE, on the working electrode immersed in the electrografting solution. The applied voltage for electrolysis can vary depending, for example, on the nature/properties of the substrate metal (e.g., reducibility or electron affinity), the dimension of the metal surface (e.g., area or shape) to be electrografted, the type of diazonium and vinyl compounds, and also on the desired quality (e.g., thickness, uniformity, etc.) of the grafted polymer film. For example, the applied voltage will be different for each individual metals, e.g., Au, Ti and Cu, and also for various size and shape of the metal layer.

In example embodiments, the polymer layer 48 can then be annealed to achieve desired cross-linking and a re-organized polymer film with the desired thickness and uniformity. For example, an anneal, which is typically performed at a high temperature such as 100 to 300° C., can result in (i) cross-linking of polymers via chemical interaction of functional groups on adjacent chains, and/or (ii) physical re-organization of attached polymer chains via substantial change in molecular motions in the main polymer and side chains, removal of trapped solvents or gas, etc.

In example embodiments, the maximum temperature at which block 18 (FIG. 1) should be annealed to form the polymer layer 48 is 250° C. The electrografting process provides a stable chemical bond between the electrically conductive metal layer 40 and the polymer layer 48. The resulting polymer layer 48 formed at the surface of the metal layer 40 can be detected, for example, by XPS and IR spectrographic techniques.

In example embodiments, the polymer layer 48 comprises a cross-linked polymer that is sensitive to water vapor. When the polymer layer 48 is exposed to water vapor, the water is absorbed into, or otherwise affects the polymer material resulting in an alteration in the permittivity (or dielectric constant) of the polymer material, which raises or lowers the capacitance of the capacitor. By monitoring the change in capacitance, the amount of water vapor (i.e., humidity) can be quantified. In example embodiments, a capacitive humidity sensor formed from a polyvinyl ester according to the disclosure, can exhibit a relatively linear capacitance response over a range of 10% to 90% relative humidity.

Figure 7:
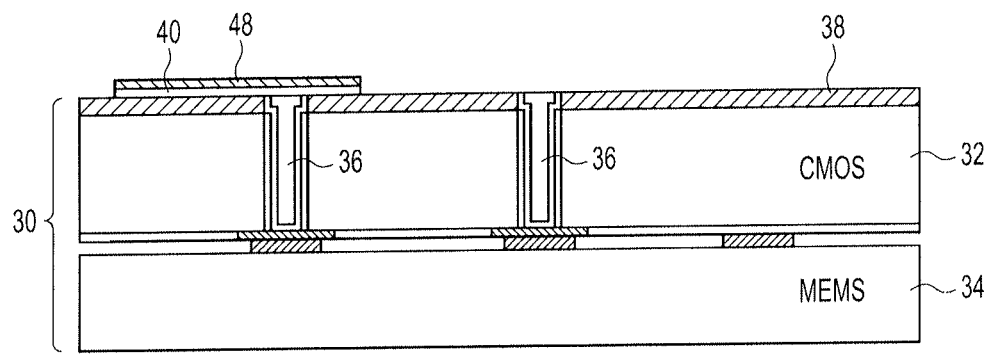
FIG. 7 is a cross-sectional, elevational view of the substrate of FIG. 5, at a subsequent process step according to the operational sequence of FIG. 1, showing the etched electrically conductive metal layer.

After forming the polymer layer 48, the operational sequence of FIG. 1 progresses to block 20 where exposed sections of the metal layer 40 are removed using the polymer layer 48 as a mask to expose the insulating layer 38 on the surface of the CMOS structure, as shown in FIG. 7. The metal layer 40 can be removed, for example, by wet etching. The procedure of block 20 (FIG. 1) can be performed at room temperature.

Figure 8:
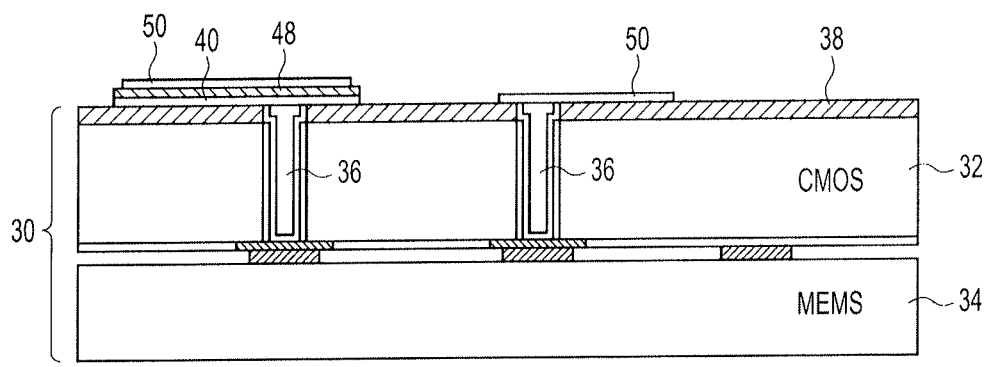
FIG. 8 is a cross-sectional, elevational view of the substrate of FIG. 7, at a subsequent process step according to the operational sequence of FIG. 1, showing the formation of a redistribution layer (RDL).

Next, at block 22 (FIG. 1), an electrically conductive material layer is formed over the substrate, for example, by sputtering or other appropriate processing technique. The conductive material layer is then processed to form a redistribution layer (RDL) 50, is shown in FIG. 8. The RDL layer 50 is generally composed of interconnects and other electrical contacts or pathways (e.g., traces, vias). The components of the RDL layer 50 can be formed using conventional substrate manufacturing processing, for example, patterning and etching. In various example embodiments, the RDL layer 50 can be formed, for example, from aluminum (Al), aluminum copper (AlCu), or another suitable electrically conductive material. The maximum temperature at which block 22 (FIG. 12) should be performed is 200° C.

Figure 9:
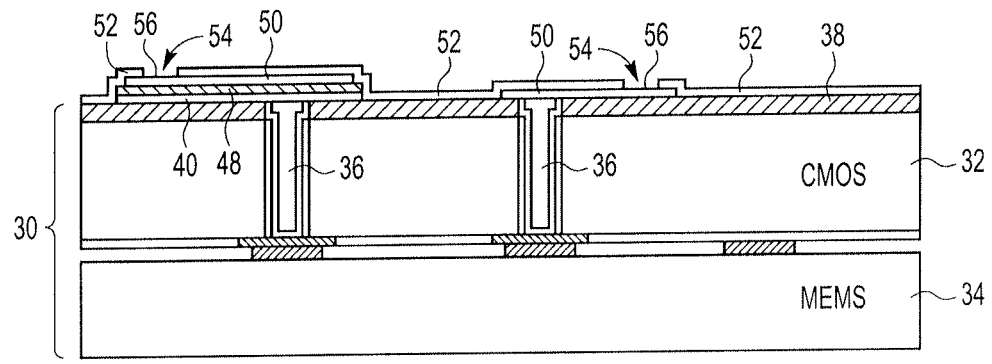
FIG. 9 is a cross-sectional, elevational view of the substrate of FIG. 8, at a subsequent process step according to the operational sequence of FIG. 1, showing the formation of a passivation layer over the RDL layer.

At block 24 (FIG. 1), an insulative layer 52 (also called a passivation layer or solder mask) is formed over the RDL layer 50, as shown in FIG. 9. As depicted, the insulative layer 52 is patterned to form one or more openings 54 to expose a contact area 56 of the RDL layer 50. The insulative layer 52 can be formed, for example, from a dielectric (insulating) material such as silicon dioxide, silicon nitride and silicon oxynitride, by any appropriate processing technique. The insulative layer 52 can be patterned and etched by a lithographic technique to expose active areas, traces and contacts of the RDL layer 50. The maximum temperature at which block 24 (FIG. 1) should be performed is 300° C.

Figure 10:
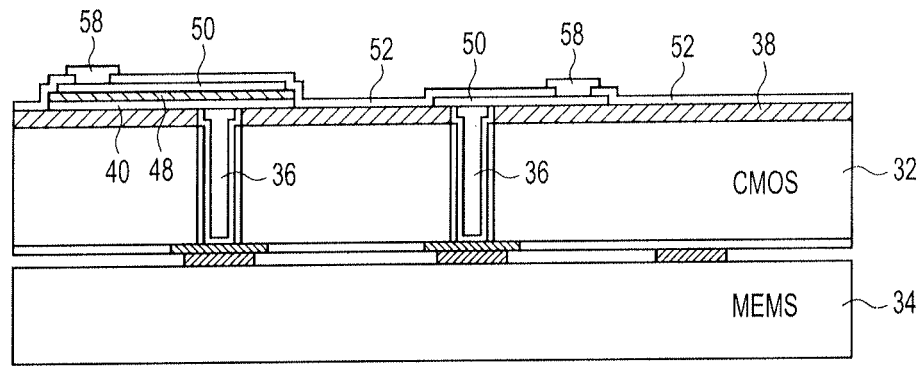
FIG. 10 is a cross-sectional, elevational view of the substrate of FIG. 9, at a subsequent process step according to the operational sequence of FIG. 1, showing the formation of an under-bump metallization (UBM) structure.

Next, at block 26 (FIG. 1), electrically conductive materials (e.g., metals) are deposited onto the exposed contact area 56 of the RDL, and patterned to form an under-bump metallization (UBM) structure 58, as shown in FIG. 10. In example embodiments, the conductive materials are composed of three metal layers, for example, copper (Cu), nickel (Ni) and titanium (Ti). The conductive material layers can be deposited, for example, using a sputtering process. The maximum temperature at which block 26 (FIG. 1) should be performed is 200° C. In example embodiments, the UBM structure 58 is bowl-shaped with a depression therein. A solder ball (not shown) can be placed on top of the UBM structure such that, after reflow, the solder bump sits inside the UBM structure.

Figure 11:
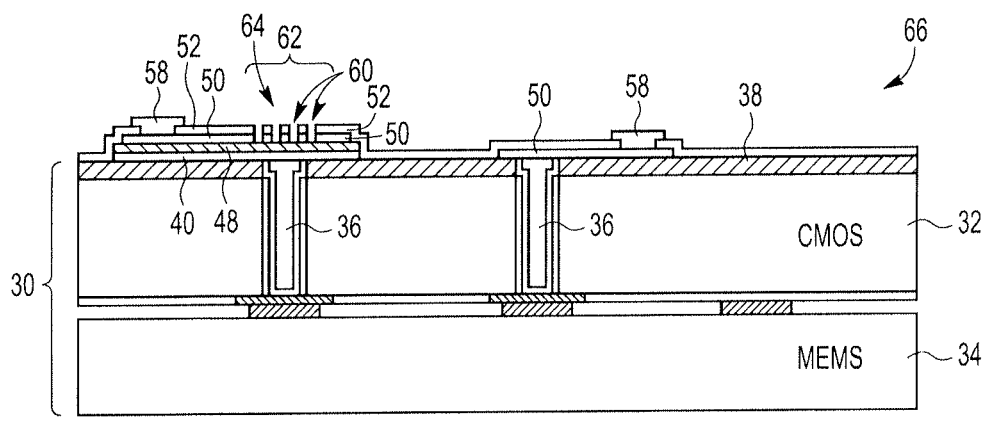
FIG. 11 is a cross-sectional, elevational view of the substrate of FIG. 10, at a subsequent process step according to the operational sequence of FIG. 1, showing the formation of openings to expose the polymer layer of the humidity sensor in the semiconductor device.

At block 28 (FIG. 1), one or more openings 60 are formed through the insulative (passivation) layer 52 and the underlying RDL layer 50, as shown in FIG. 11, to expose the polymer layer 48 within a humidity sensing area 62 to the ambient air. The exposed polymer layer 48, which is composed of a moisture-sensitive polymer, functions as a capacitive humidity sensing element. The capacitive humidity sensor is composed of the moisture-sensitive polymer layer 48 (as the sensing element) situated between metal layer 40 as the bottom electrode and RDL layer 50 as the top electrode.

The openings 60 can be formed, for example, by dry-etching the passivation layer 52 and wet-etching the RDL layer 50. The process of block 28 (FIG. 1) can be performed at room temperature.

The resulting semiconductor device 66 comprises a moisture-sensitive polymer layer 48 electrografted to an electrically conductive metal layer 40 situated on an IC substrate 30, and exposed within openings 62 through a passivation layer 52 and the RDL layer 50 such that the moisture-sensitive polymer layer 48 functions as a capacitive humidity sensor 64 when exposed to ambient air. Thus, in some example embodiments, the capacitive humidity sensor 64 is composed of the electrically conductive metal layer 40 as a bottom electrode and the RDL layer 50 as a top electrode.

Figure 12:
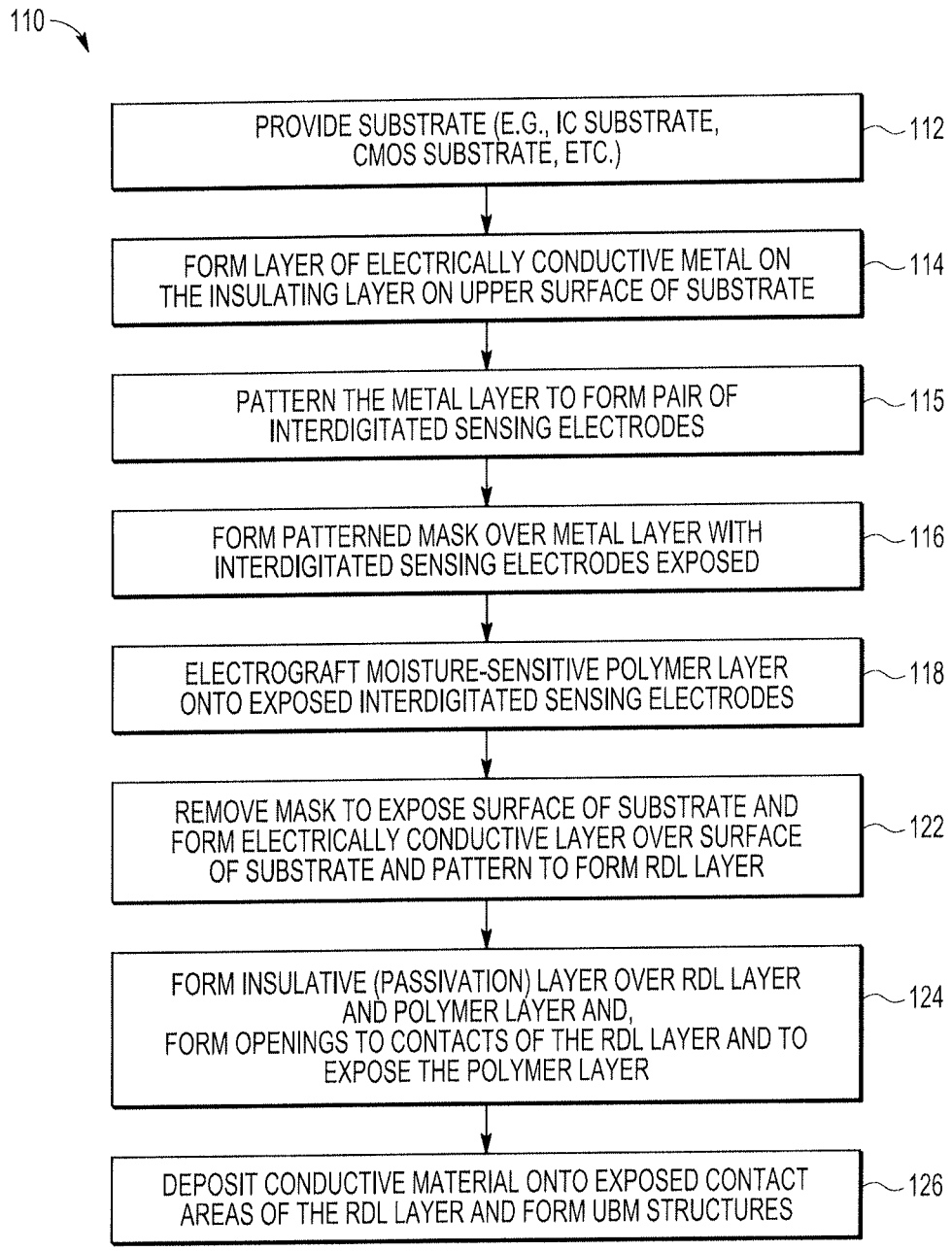
FIG. 12 is flow diagram illustrating a fabrication sequence to construct a capacitive humidity sensor according to another example embodiment of the invention, given by way of example.

FIG. 12 is a flowchart showing an example embodiment of a second low-temperature procedure 110 for fabricating a capacitive humidity sensor on an integrated circuit (IC) substrate according to example embodiments of the present disclosure. FIGS. 13 to 19 illustrate cross-sectional side views of a semiconductor device at various stages of manufacture according to the process flow shown in FIG. 12.

The procedure commences at block 112 where a substrate 130 (FIG. 13) is provided. As illustrated, in example embodiments, the substrate 130 can be in the form of a CMOS substrate 132 that is bonded to a MEMS substrate 134. As shown, the CMOS substrate 132 is structured with an insulating layer 138 (e.g., silicon oxide, SiO) on an upper surface. The CMOS substrate 132 can include a plurality of conductive through-silicon vias (TSVs) 136 that extend through the CMOS substrate 132. In another example embodiment, the MEMS substrate 134 is absent, and the capacitive humidity sensor can be fabricated using the CMOS substrate 132 as the substrate 130.

Figure 13:
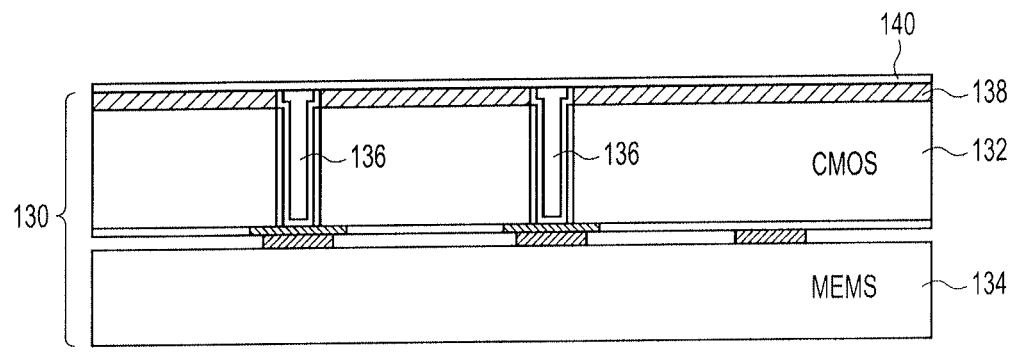
FIG. 13 is a cross-sectional, elevational view of an exemplary substrate for use with the procedure illustrated in FIG. 12, showing an electrically conductive metal layer formed on an insulative layer on the substrate.

Next, at block 114 (FIG. 12), an electrically conductive metal layer 140 is formed on the insulating layer 138 on the upper surface of the CMOS substrate 132, as shown in FIG. 13, similar to the formation of metal layer 40 (FIG. 3). The conductive metal layer 140 is a metal material (e.g Ti, Pt, Au, etc.) to which an organic material layer (e.g., polymer) layer) can be attached through an electrografting process as described herein. The maximum temperature at which block 114 (FIG. 13) should be performed is 200° C.

Figure 14:
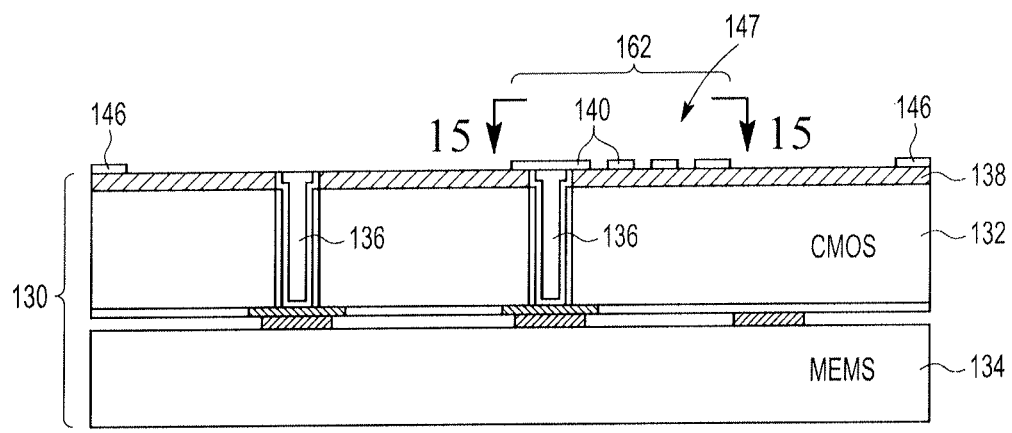
FIG. 14 is a cross-sectional, elevational view of the substrate of FIG. 13, at a subsequent process step according to the operational sequence of FIG. 12, showing the electrically conductive metal layer patterned to form a pair of interdigitated sensor electrodes.
Figure 15:
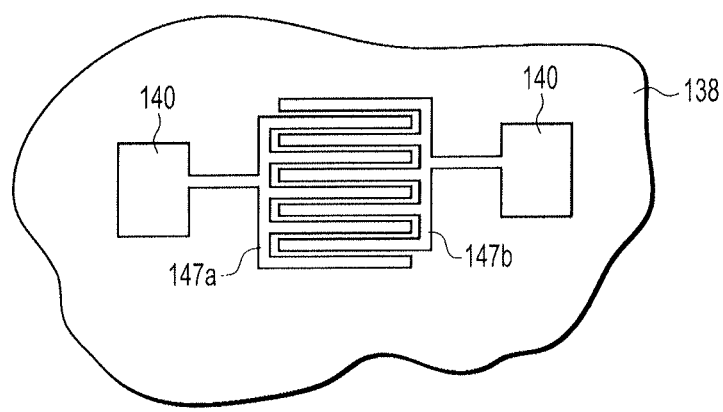
FIG. 15 is a top plan view of the interdigitated sensor electrodes of FIG. 14, taken along lines 15-15.

The operational sequence 110 (FIG. 12) progresses to block 115 where the conductive metal layer 140 is patterned into a pair of interdigitated sensing electrodes 147a, 147b, as shown in FIGS. 14 and 15. The interdigitated sensing electrodes 147a, 147b are positioned in a humidity sensing region 162 of the CMOS substrate 132.

As shown in FIG. 15, the pair of sensing electrodes 147a, 147b are composed of two sets of interdigitated fingers or extensions. The set of fingers on a first side (e.g., the left side) forms one sensing electrode 147a, and the set of fingers on a second side (e.g., the right side) forms the other sensing electrode 147b. Sensing electrodes 147a, 147b function as opposite electrodes of the capacitor with the capacitance of the capacitor changing according to the humidity level.

The metal layer 140 is also patterned such that electrically conductive contacts 146 are provided at each edge on the upper surface of the CMOS substrate 132. The electrical contacts 146 are connected to the metal layer 140 and provide a single electric potential to the sensing electrodes 147a, 147b for the electrografting process.

The process of block 115 (FIG. 12) can be performed at room temperature.

Figure 16:
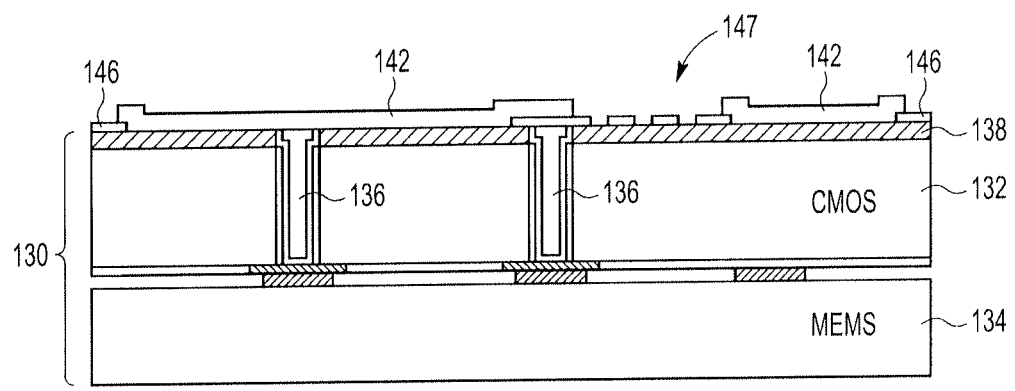
FIG. 16 is a cross-sectional, elevational view of the substrate of FIG. 14, at a subsequent process step according to the operational sequence of FIG. 12, showing the formation of a patterned photoresist mask over portions of the electrically conductive metal layer and the substrate.

The operational sequence 110 (FIG. 12) progresses to block 116 where a patterned mask 142 (e.g., photoresist, etc.) is formed over the conductive metal layer 140, as shown in FIG. 16. The patterned mask 142 includes openings exposing the pair of interdigitated sensing electrodes 147a, 147b onto which an organic layer (e.g., polymer layer) is to be electrografted. The patterned mask (photoresist) layer 142 is applied such that at least a portion of the first and second electrical contact points 146 are left exposed at the edges of the substrate 130. The procedure of block 116 should be performed at a maximum temperature of 120° C.

Figure 17:
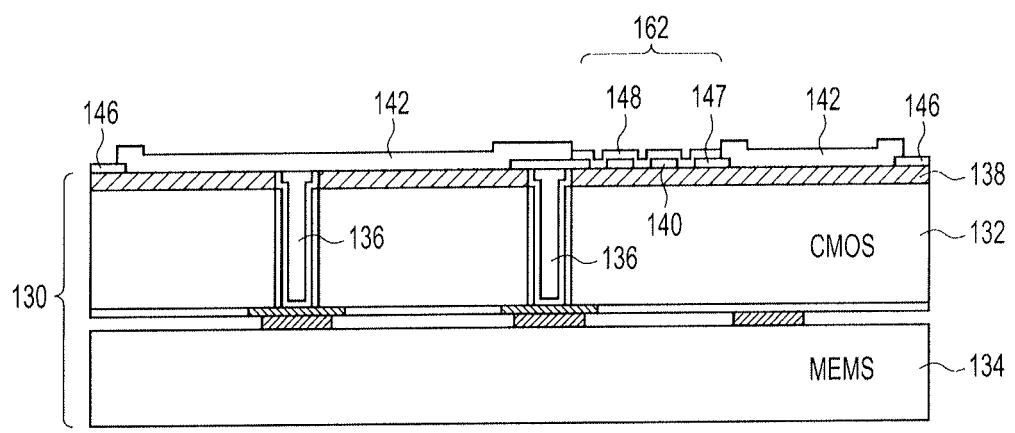
FIG. 17 is a cross-sectional, elevational view of the substrate of FIG. 16, at a subsequent process step according to the operational sequence of FIG. 12, showing the formation of a polymer layer by electrografting on the unmasked portions of the interdigitated sensing electrodes.

Next, at block 118 (FIG. 12), an organic (e.g., polymer) layer 148 is formed on the unmasked and exposed interdigitated sensing electrodes 147a, 147b by an electrografting process, as depicted in FIG. 17. In example embodiments, the polymer layer 148 comprises a cross-linked polymer that is sensitive to water vapor (humidity) whereby exposure to water vapor will alter the dielectric properties of the polymer material. By monitoring the change in capacitance, the relative humidity of the environment can be quantified.

In an example embodiment according to the disclosure, in a first step in an electrografting process, an aqueous acidic electrografting composition comprising water (as solvent), an aryldiazonium salt, a vinyl compound and an acidic component (to maintain pH=1 to 2), as described with regard to FIG. 5 (block 18 of FIG. 1 is applied to the exposed electrodes 147a, 147b.

In the illustrated example embodiment, the electrografting process is performed on the exposed area of the sensing electrodes 147a, 147b on the assembly shown in FIG. 16. An electrochemical cell for carrying out this electrografting process will be composed of (i) a working electrode, which in the illustrated example embodiment, is the sensing electrodes 147a, 147b of the metal layer 140 (including the whole assembly as shown in the FIG. 16). An electrochemical cell for carrying out this electrografting process will be composed of (i) a working electrode, which in the illustrated example embodiment, is the metal layer 40 (including the whole assembly as shown in the FIG. 5), (ii) a counter electrode of inert platinum (Pt) or suitable platinized metal (external system to complete the electric circuit for electrografting; not a component of the assembly shown in FIG. 5), (iii) the electrografting solution applied between the working and the counter electrode, and (iv) an external power supply providing desired electrical potentials to the metal layer 40 (working electrode) through contact points 46 and to the external counter electrode (Pt or platinized metal).

In an example embodiment, the electrografting solution/composition can be prepared by mixing the individual components (e.g., vinyl monomer, aryldiazonium cation and acidic components) in a dedicated mixing system (e.g., mixing chamber, beaker, etc.). The electrografting composition can then be applied between the working and counter electrodes by using an appropriate transfer system (e.g., beaker or other transfer vessel or apparatus).

In example embodiments, the electrografting process can be conducted by applying a desired potential (using external power supply) for a specific period of time across the sensing (working) electrode 147a, 147b and the counter electrode through the electrografting composition (e.g., solution comprising vinyl compound, aryldiazonium salt, and the acidic components), whereby electroreduction of the diazonium cation ($ArN_2^+$) from the solution forms aryl radicals. The aryl radicals chemically bond on one end to the surface of the sensing electrodes 147a, 147b to form a primer layer. On the other end, the aryl radicals initiate polymerization of the vinyl compound to form the polymer layer 148.

The electrolysis can be performed by applying an electrical potential of −1V/SCE on the working electrode immersed in the electrografting solution. The applied voltage for electrolysis can vary depending, for example, on the nature/properties of the substrate metal (e.g., reducibility or electron affinity), the dimension of the metal surface (e.g., area or shape) to be electrografted, the type of diazonium and vinyl compounds, and also on the desired quality (e.g., thickness, uniformity, etc.) of the grafted polymer film. For example, the applied voltage will be different for each individual metals, e.g., Au, Ti and Cu, and also for various size and shape of the metal layer.

As the growth of the polymer layer 148 proceeds around the surface of the interdigitated electrodes 147a, 147b, gap and voids between the interdigitated electrodes 147a, 147b are filled in and bridged by the polymer layer 148. In example embodiments, the polymer layer 148 can range in thickness from 10 to 1000 nm. In example embodiments, the reaction leads to a layer of the polyvinyl ester polymer over a primer layer bonded to the surface of the metal layer 140.

In example embodiments, the polymer layer 148 can then be annealed to achieve desired cross-linking and a re-organized polymer film with the desired thickness and uniformity. For example, as discussed above, an anneal, which is typically performed at a high temperature such as 100 to 300° C., can result in (i) cross-linking of polymers via chemical interaction of functional groups on adjacent chains, and/or (ii) physical re-organization of attached polymer chains via substantial change in molecular motions in the main polymer and side chains, removal of trapped solvents or gas, etc. In various example embodiments, the polymer layer 148 comprises a humidity-sensitive polymer. In example embodiments, the maximum temperature at which block 118 (FIG. 12) should be performed is 250° C. (for annealing the polymer layer).

Figure 18:
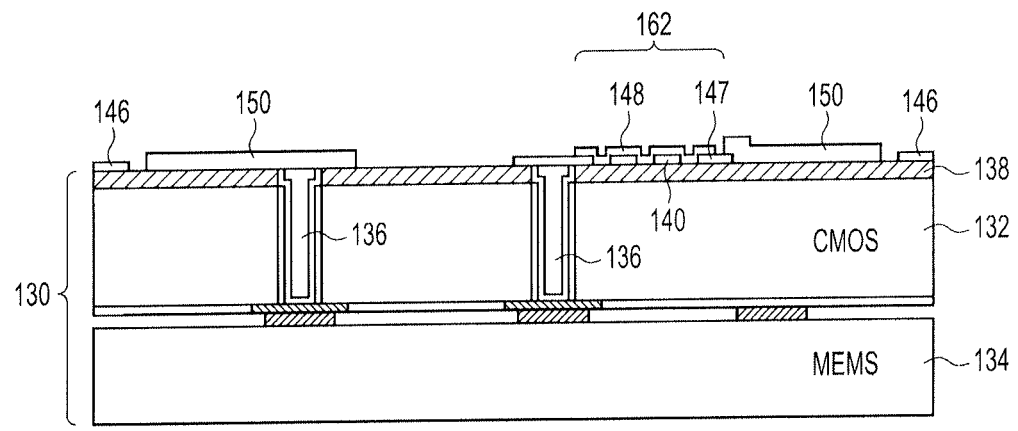
FIG. 18 is a cross-sectional, elevational view of the substrate of FIG. 17, at a subsequent process step according to the operational sequence of FIG. 12, showing removal of the mask and the formation of an RDL layer.

After forming the polymer layer 148, the operational sequence of FIG. 12 progresses to block 122 wherein the photoresist mask is removed and a redistribution layer (RDL) 150 can be formed over the substrate, as shown in FIG. 18. The RDL layer 150 can be formed, for example, by applying an electrically conductive material layer over the substrate (e.g., by sputtering or other processing technique) and then patterning (e.g., by wet etching) to form interconnects and other electrical contacts or pathways (e.g., traces, vias) as described with regard to FIG. 8 (block 22 of FIG. 1). The maximum temperature at which block 122 (FIG. 12) should be performed is 200° C.

Figure 19:
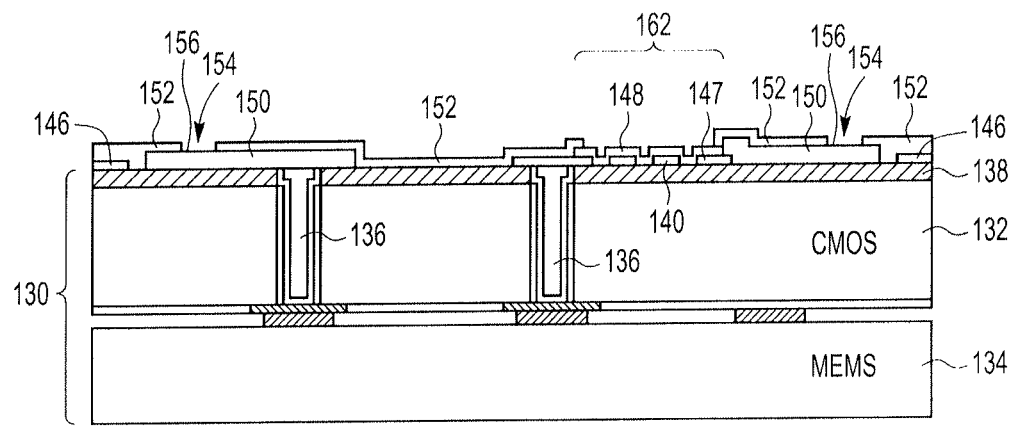
FIG. 19 is a cross-sectional, elevational view of the substrate of FIG. 18, at a subsequent process step according to the operational sequence of FIG. 12, showing the formation of a passivation layer on portions of the RDL layer.

At block 124 (FIG. 12), an insulative layer 152 (e.g., a passivation layer) 52, as shown in FIG. 19, is then formed over the substrate, and patterned to provide openings 154 to contact areas 156 of the RDL layer 150, and to expose the polymer layer 148 within the humidity sensing area 162. The insulative layer 152 (e.g., passivation layer) can be formed and patterned as described with regard to FIG. 9 (block 24 of FIG. 1). The maximum temperature at which block 124 (FIG. 12) should be performed is 300° C.

Figure 20:
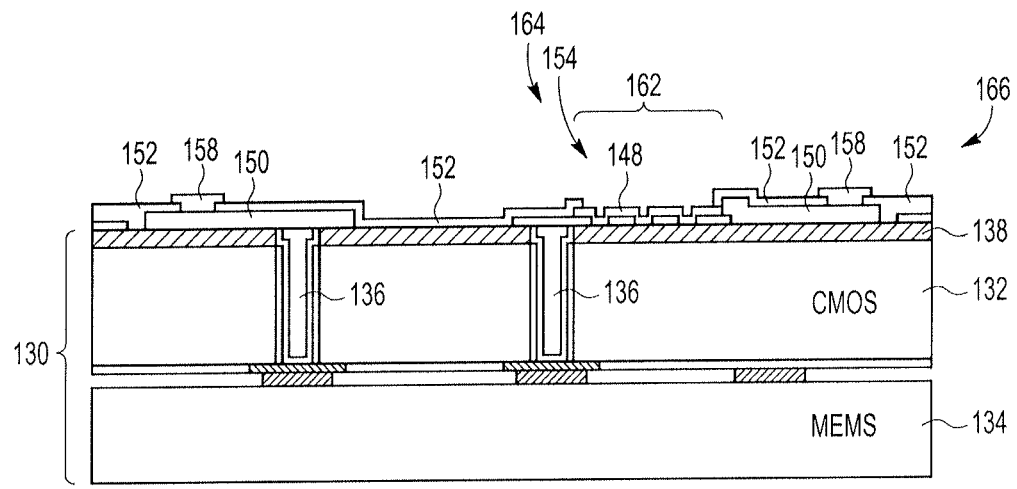
FIG. 20 is a cross-sectional, elevational view of the substrate of FIG. 19, at a subsequent process step according to the operational sequence of FIG. 12, showing the formation of an under-bump metallization (UBM) structure, and the resulting device incorporating a capacitive humidity sensor.

Next, at block 126 (FIG. 12), an under-bump metallization (UBM) structure 158, as shown in FIG. 20, can be formed on the exposed contact area 156 of the RN, layer 150, as described with regard to FIG. 10 (block 26 of FIG. 1). A sputtering process can be used to deposit the metal layer for the UBM structure 158. The maximum temperature at which block 126 (FIG. 12) should be performed is 200° C. In an example embodiment, a solder ball (not shown) can be mounted on the UBM structures.

The resulting semiconductor device 166 comprises a moisture-sensitive polymer layer 148 electrografted to a pair of interdigitated sensing electrodes 147a, 147b of an electrically conductive metal layer 140 situated on an IC substrate 130, and exposed within an opening 154 in a passivation layer 152 such that the moisture-sensitive polymer layer 148 functions as a capacitive humidity sensor 164 when exposed to ambient air.

Although the procedures of FIGS. 1 and 12 are described in the context of capacitive humidity sensors, it should be understood that those procedures are also applicable to capacitive sensors that are configured for sensing chemical substances (e.g., gases) other than water vapor. For these applications, a polymer for sensing a particular chemical or category of chemicals, for example, sulfur oxides $SO_x$ (e.g., $SO_2$, $SO_3$, etc.), and gaseous nitrogen oxides $NO_x$ (e.g., NO, $N_2O$, $NO_2$, $N_2O_5$, etc.), is formed by electrografting according to the disclosure. Examples of such polymers include, for example, polyvinyl methacrylates, polyvinyl benzoates, vinyl cinnamates, polyvinyl chrotonate, and polymethyl methacrylates, etc., as used for humidity sensors. Variations can be made in the cross-linked polymer structures (e.g., pore size, etc., specific for the physical absorption of gas molecules of particular size and shape) via suitable control of the number and nature of the functional groups on the polymer chain and thereby controlling interactions between the functional groups on adjacent polymer chains during a post-electrografting anneal step.

Figure 21:
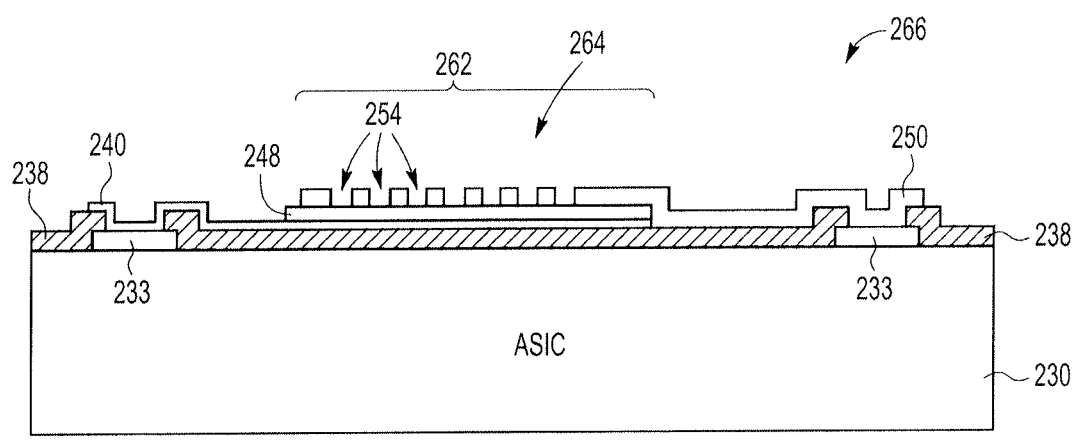
FIG. 21 is a cross-sectional, elevational view of a capacitive humidity sensor fabricated on an application-specific integrated circuit (ASIC) substrate according to another example embodiment of the disclosure.

FIG. 21 illustrates another example embodiment of a capacitive humidity sensor 264 fabricated according to an example embodiment of the disclosure on a substrate 230 composed of an application-specific integrated circuit (ASIC), without TSVs or a MEMS substrate. As illustrated, the ASIC substrate 230 includes an insulating layer 238 and contact pads 233 on an upper surface. An electrically conductive metal layer 240 is formed over one of the contact pads 233 and a portion of the insulating layer 238. The metal layer 240 is then covered by a patterned mask (not shown) and an organic layer 248 (e.g., a moisture-sensitive polymer layer) is electrografted to an exposed area of the conductive metal layer 240 as described herein. A second electrically conductive material layer 250 is then formed over the substrate, a contact pad 233, and the polymer layer 248. The conductive material layer 250 is patterned (e.g., by etching) to form components of an RDL layer and openings 254 therethrough to expose the polymer layer 248. The resulting device 266 includes a capacitive humidity sensor 264 is composed of the moisture-sensitive polymer layer 248 exposed within the openings 254 to the ambient air within a humidity sensing region 262.

Figure 22:
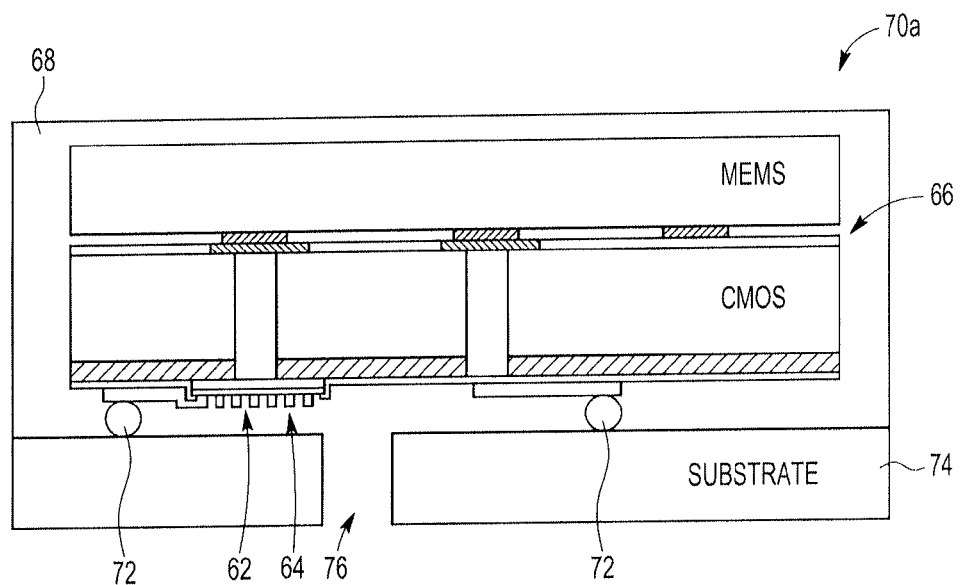
FIG. 22 is a cross-sectional, elevational view of an example embodiment of semiconductor device package according to the disclosure.
Figure 23:
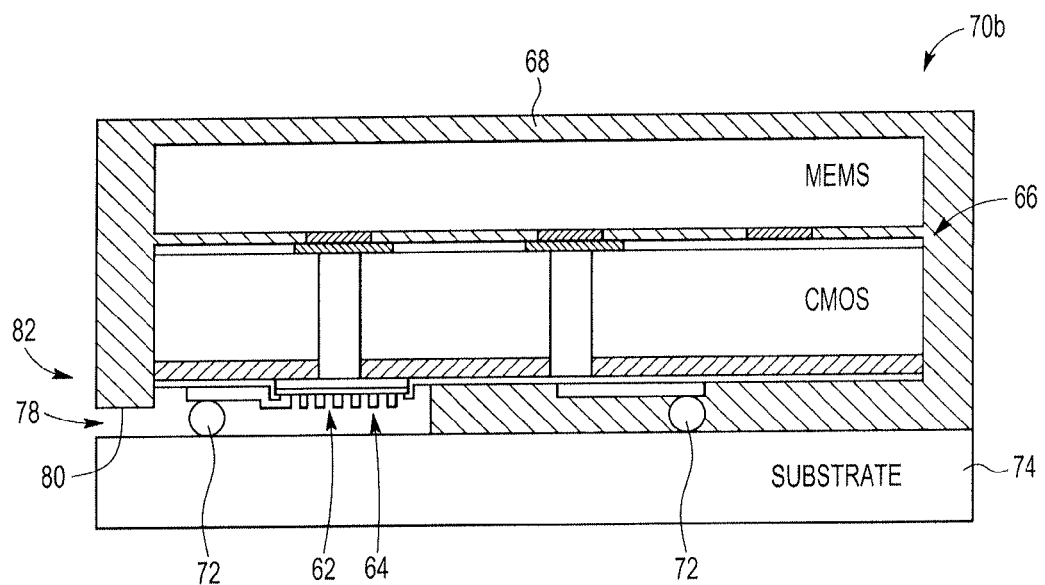
FIG. 23 is a cross-sectional, elevational view of another example embodiment of semiconductor device package according to the disclosure.

In example embodiments, as illustrated in FIGS. 22 and 23 showing the semiconductor device 66 (FIG. 11) prepared according to the process of FIG. 1 as an example, an encapsulation process can be performed to cover the device 66 with a mold compound or mold encapsulant 68, which is then cured, to produce a semiconductor device package 70a, 70b. The semiconductor device package 70a, 70b includes the capacitive humidity sensor 64 formed on and exposed at the surface of an encapsulated IC substrate (e.g., CMOS, ASIC, etc.). The molding material can be any appropriate encapsulant, for example, a silica-filled epoxy molding compound, a plastic encapsulation resin, or other polymeric material such as silicones, polyimides, phenolics and polyurethanes. Encapsulation of the device 66 can be conducted, for example, by transfer molding, stencil printing, compression molding, and the like.

As shown in FIGS. 22 and 23, a portion of the device 66 including the capacitive humidity sensor 64 is not covered by the mold compound/encapsulant 68. External contacts 72 (e.g., solder bumps) can be attached onto the UBM structures 58 of the device and mounted on a substrate 74 such as a PCB or other external circuitry.

In the example embodiment of the device package 70a shown in FIG. 22, the substrate 74 (e.g., PCB, etc.) is structured with an opening 76 extending therethrough through which the capacitive humidity sensor 64 is exposed to ambient air. In another example embodiment shown in FIG. 23, an opening or gap 78 is provided between the surface 80 of the encapsulant 68 covering the device package 70b and the substrate 74 (e.g., PCB, etc.) such that the capacitive humidity sensor 64 is exposed to the ambient air through the opening or gap 78 along a side 82 of the package 70 mounted on the substrate 74 (e.g., PCB, etc.).

In various example embodiments, devices and packages comprising the capacitive humidity sensor, and the methods of forming the capacitive humidity sensor, as described herein or otherwise encompassed herein, can be used in networking systems, automotive systems, smart phones, agriculture monitoring systems, and other applications.

Figure 24:
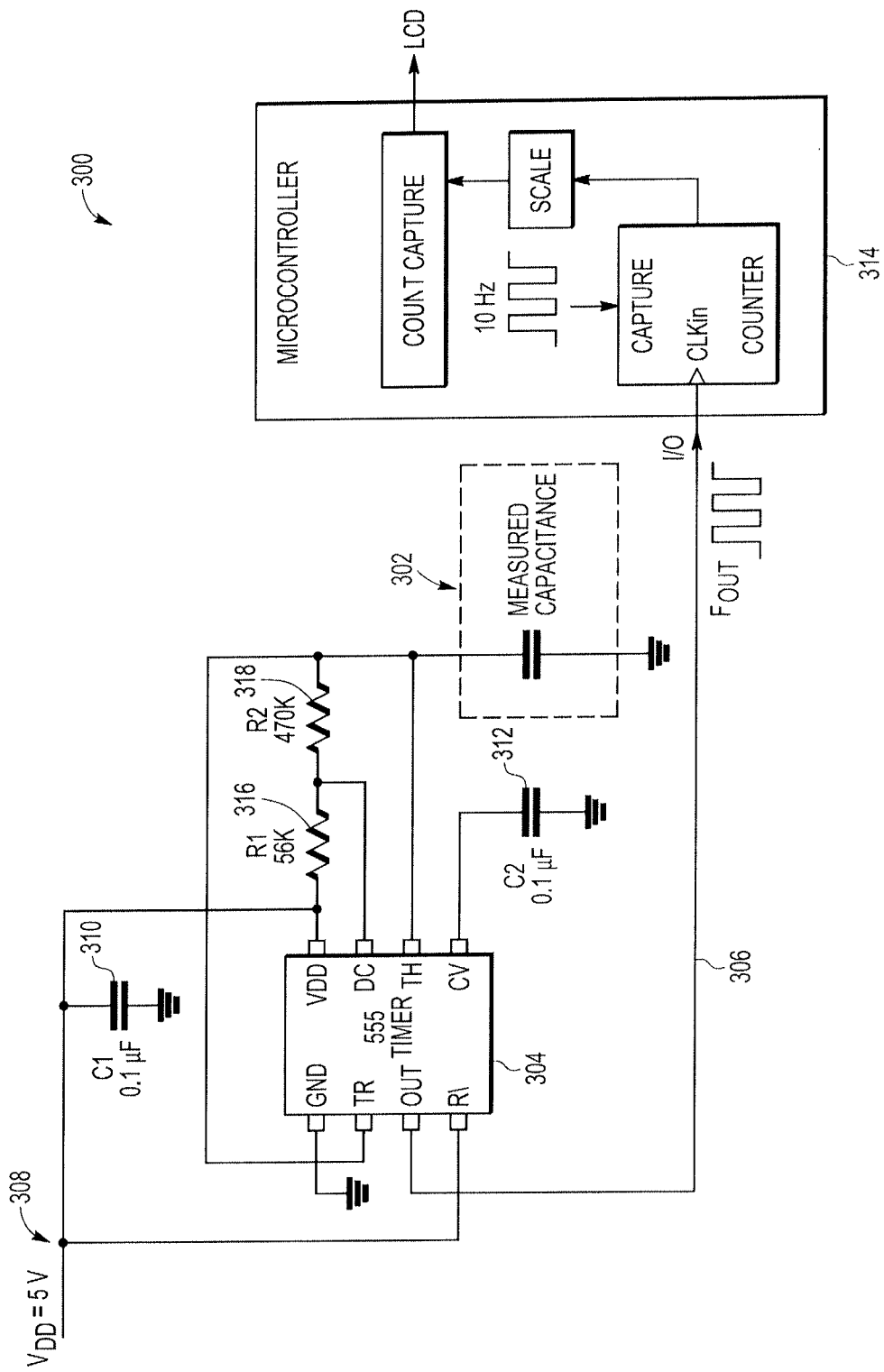
FIG. 24 is a schematic diagram of an illustrative electronic circuit for reading a capacitive humidity sensor to determine a level of sensed humidity.

FIG. 24 is a schematic diagram of an example embodiment of an electronic circuit 300 for reading a capacitive humidity sensor 302 according to the disclosure to determine a level of sensed ambient humidity. Digitizing the value of a capacitive sensor may involve generating a frequency that is inversely proportional to a capacitance C of the capacitive humidity sensor 302 and counting pulses over a fixed period of time to determine the frequency. In the configuration of FIG. 24, an analog timer circuit 304 is used to generate an output signal 306 with a frequency $F_{OUT}$. The analog timer circuit 304 operates from a voltage supply $V_{DD}$ 308 of 5 volts. A first capacitor C1 310 functions as a bypass, shunting any alternating current components on $V_{DD}$ 308 to ground. A second capacitor C2 312 also functions as a bypass, shunting any alternating current components on a control voltage CV terminal of the analog timer circuit 304 to ground.

The frequency $F_{OUT}$ of the analog timer circuit 304 is inversely proportional to a capacitance C provided by the capacitive humidity sensor 302. A microcontroller 314 is configured to count pulses of the output signal 306 within a given period of time to calculate a frequency for $F_{OUT}$. A first resistor R1 316 and a second resistor R1 318 function as a voltage divider and are selected based upon the capacitance provided by the capacitive humidity sensor 302. The basic equation relating the capacitance C provided by the capacitive humidity sensor and frequency $F_{OUT}$ is: $F_{OUT}=1/C*(R1+2*R2)*\ln 2)$.

The frequency for $F_{OUT}$ is proportional to a level of humidity sensed by the capacitive humidity sensor 302. For illustrative purposes only, the values of C1 310 and C2 312 may each be approximately 0.1 microfarads, the value of R1 316 may be approximately 56 kilohms, the value of R2 318 may be approximately 470 kilohms, and the analog timer circuit 304 may be a 555 timer integrated circuit (IC). The circuit 300 of FIG. 23 is provided for illustrative purposes only, as any of various approaches may be used to read the capacitive humidity sensor 302. One characteristic of the circuit 300 of FIG. 23 is that there is no requirement for an analog-to-digital converter (ADC) or comparator in the microcontroller 314.

The terms "top," "bottom," "upper," "lower," "over," "under," "overlying," "underlying" and the like in the description and in the claims, if any, are used for descriptive purposes and not necessarily for describing permanent relative positions. It is understood that the terms so used are interchangeable under appropriate circumstances such that the example embodiments of the invention described herein are, for example, capable of operation in other orientations than those illustrated or otherwise described herein.

The terms "a" or "an," as used herein, are defined as one or more than one. Also, the use of introductory phrases such as "at least one," "at least two," and "one or more" in the claims should not be construed to imply that the introduction of another claim element by the indefinite articles "a" or "an" limits any particular claim containing such introduced claim element to devices, etc., containing only one such element, even when the same claim includes the introductory phrases "one or more" or "at least one" and indefinite articles such as "a" or "an." The same applies to the use of definite articles.

Although the invention is described herein with reference to specific example embodiments, various modifications and changes can be made without departing from the scope of the present invention as set forth in the claims below. Accordingly, the specification and figures are to be regarded in an illustrative rather than a restrictive sense, and all such modifications are intended to be included within the scope of the present invention. Any benefits, advantages, or solutions to problems that are described herein with regard to specific example embodiments are not intended to be construed as a critical, required or essential feature or element of any or all of the claims.

What is claimed:

1. A method for forming a semiconductor device, comprising:
    forming a first electrically conductive metal layer on a surface of an IC substrate;
    electrografting a moisture-sensitive polymer layer onto the first electrically conductive metal layer;
    forming a passivation layer over the substrate with the polymer layer exposed through one or more openings in the passivation layer;
    wherein the polymer layer functions as a capacitive humidity sensing element when exposed to ambient air;
    further comprising, prior to electrografting the polymer layer,
        forming the first electrically conductive metal layer over an insulating layer on the substrate; and forming a patterned mask over the first electrically conductive metal layer;
    wherein the polymer layer is electrographed onto an exposed area of the first electrically conductive metal layer;
    further comprising, after electrografting the polymer layer, selectively removing the mask and conductive metal layer underlying the mask to expose the insulating layer on the substrate;
    patterning the first electrically conductive metal layer to form an RDL layer comprising a contact area;
    forming a passivation layer over the RDL layer;
    forming an opening through the passivation layer to expose the contact area of the RDL layer;
    forming a UBM structure on the contact area within the opening; and
    forming a plurality of openings through the passivation layer and the RDL layer underlying the passivation layer to expose the polymer layer;
    wherein the polymer layer functions as a capacitive humidity sensing element when exposed to ambient air;
    further comprising, prior to electrografting the polymer layer,
    forming the first electrically conductive metal layer over an insulating layer on the substrate; and
    masking and patterning the first electrically conductive metal layer to form a pair of interdigitated sensing electrodes; and
    forming a patterned photoresist mask over the substrate with the interdigitated sensing electrodes exposed;
    wherein the polymer layer is electrographed onto the exposed interdigitated sensing electrodes.

2. The method of claim 1, wherein the electrografting comprises:
    applying an aqueous acidic electrografting composition to a surface of the first electrically conductive metal layer, wherein the composition comprises a solvent, an aryldiazonium salt, a vinyl ester monomer compound and an acidic component to maintain a pH of 1 to 2; and
    applying an electric potential to the surface of the metal layer to form a primer layer of aryl radicals, followed by addition and polymerization of vinyl monomers onto the primer layer to form an electrografted polymer layer on the surface of the metal layer.

3. The method of claim 2, wherein the polymer layer comprises a polyvinyl ester.

4. The method of claim 3, wherein the polyvinyl ester is selected from the group consisting of polyvinyl methacrylate (PVM), polyvinyl benzoate (PVG), polyvinyl crotonate (PVCr), polyvinyl cinnamate (PVCi), and polymethyl methacrylate (PMMA), and
    the polyvinyl ester comprises functional groups selected from the group consisting of carboxyl (—COOH), hydroxyl (—OH) and amino (—NH$_2$) groups.

5. The method of claim 1, wherein the first electrically conductive metal layer comprises a pair of interdigitated sensing electrodes, and the polymer layer is electrographed to the pair of sensing electrodes.

6. The method of claim 1, wherein the first electrically conductive metal layer comprises a metal selected from the group consisting of titanium, platinum, and gold, and combinations thereof.

7. The method of claim 1, wherein the IC substrate comprises a CMOS substrate or an ASIC substrate.

8. A semiconductor device, comprising:
    a moisture-sensitive polymer layer electrografted to a first electrically conductive metal layer situated on an IC substrate, and exposed within one or more openings through a passivation layer;

wherein the moisture-sensitive polymer layer functions as a capacitive humidity sensing element when exposed to ambient air;
wherein the IC substrate comprises an insulative layer on an upper surface;
the first electrically conductive metal layer over the insulative layer;
the moisture-sensitive polymer layer electrografted to the first electrically conductive metal layer;
an RDL layer overlying portions of the moisture-sensitive polymer layer;
wherein the passivation layer is over the RDL layer;
one or more of openings through the passivation layer and the RDL layer configured to expose the moisture-sensitive polymer layer;
wherein the openings extend through the passivation layer and underlying RDL layer with the moisture-sensitive polymer layer exposed within the openings to ambient air;
wherein the moisture-sensitive polymer layer functions as a capacitive humidity sensing element;
wherein the moisture-sensitive polymer layer is electrographed to a pair of interdigitated sensing electrodes;
wherein the moisture-sensitive polymer layer is exposed within the openings through the passivation layer and the RDL layer underlying the passivation layer.

9. The semiconductor device of claim 8, wherein the semiconductor device is encapsulated as a package;
wherein an encapsulation process performed to cover the semiconductor device with a mold compound or mold encapsulant, which is then cured to produce the package.

10. The semiconductor device of claim 9, wherein the package includes an opening for passage of ambient air to the moisture-sensitive polymer layer.

11. The semiconductor device of claim 10, wherein the opening is situated along a side of the package as a space between the encapsulated semiconductor device and a substrate.

12. A method for forming a semiconductor device, comprising:
forming a first electrically conductive metal layer on a surface of an IC substrate;
electrografting a moisture-sensitive polymer layer onto the first electrically conductive metal layer; and
forming a passivation layer over the substrate with the polymer layer exposed through one or more openings in the passivation layer;
wherein the polymer layer functions as a capacitive humidity sensing element when exposed to ambient air;
further comprising, prior to electrografting the polymer layer, forming the first electrically conductive metal layer over an insulating layer on the substrate; and
masking and patterning the first electrically conductive metal layer to form a pair of interdigitated sensing electrodes; and
forming a patterned photoresist mask over the substrate with the interdigitated sensing electrodes exposed;
wherein the polymer layer is electrographed onto the exposed interdigitated sensing electrodes;
further comprising, after electrografting the polymer layer, removing the mask to expose the insulating layer on the substrate;
patterning the first electrically conductive metal layer to form an RDL layer comprising a contact area;
forming a passivation layer over the RDL layer and the polymer layer;
forming an opening through the passivation layer to expose the contact area of the RDL layer and the polymer layer; and
forming a UBM structure on the contact area within the opening; wherein the polymer layer functions as a capacitive humidity sensing element when exposed to ambient air;
further comprising, prior to electrografting the polymer layer,
forming the first electrically conductive metal layer over an insulating layer on the substrate; and
masking and patterning the first electrically conductive metal layer to form a pair of interdigitated sensing electrodes;
wherein the polymer layer is electrographed onto the interdigitated sensing electrodes.

* * * * *